United States Patent
Zweymuller

(10) Patent No.: US 7,494,510 B2
(45) Date of Patent: Feb. 24, 2009

(54) LEAFLIKE SHAFT OF A HIP-JOINT PROSTHESIS FOR ANCHORING IN THE FEMUR

(75) Inventor: Karl Zweymuller, Vienna (AT)

(73) Assignee: Smith and Nephew Orthopaedics AG, Rotkreuz (CH)

( * ) Notice: Subject to any disclaimer, the term of this patent is extended or adjusted under 35 U.S.C. 154(b) by 40 days.

(21) Appl. No.: 11/433,067

(22) Filed: May 12, 2006

(65) Prior Publication Data

US 2006/0276904 A1  Dec. 7, 2006

Related U.S. Application Data

(60) Continuation-in-part of application No. 10/355,385, filed on Jan. 30, 2003, now Pat. No. 7,175,668, which is a division of application No. 09/548,166, filed on Apr. 13, 2000, now Pat. No. 6,540,788.

(51) Int. Cl.
  *A61F 2/36* (2006.01)
(52) U.S. Cl. ............... 623/23.35; 623/23.15; 606/85
(58) Field of Classification Search .... 623/23.15–23.47
  See application file for complete search history.

(56) References Cited

U.S. PATENT DOCUMENTS

| | | | |
|---|---|---|---|
| 3,064,645 | A | 11/1962 | Ficat et al. |
| 3,067,740 | A | 12/1962 | Haboush |
| 4,199,824 | A | 4/1980 | Niederer |
| 4,359,785 | A | 11/1982 | Niederer |
| 4,404,693 | A | 9/1983 | Zweymuller |

(Continued)

FOREIGN PATENT DOCUMENTS

AT          391 264 B         9/1990

(Continued)

OTHER PUBLICATIONS

Final Office Action in related U.S. Appl. No. 09/958,463, mailed Oct. 21, 2005.

(Continued)

*Primary Examiner*—Bruce E Snow
(74) *Attorney, Agent, or Firm*—Knobbe, Martens, Olson & Bear LLP

(57) ABSTRACT

The present invention relates in certain embodiments to components of a hip-joint prosthesis. More particularly, embodiments of the invention relate to a leaf-like femoral shaft for use as part of a hip-joint prosthesis, and instruments (e.g., a rasp) and methods for implanting the shaft. The shaft includes an anchoring section extending between a proximal region and a distal end of the shaft. The shaft has a cross-sectional contour that defines a lateral side, a medial side, an anterior side and a posterior side. A corresponding rasp is preferably provided for each femoral shaft. The rasp is inserted into the femur to form a cavity having generally the same configuration as the rasp. The shaft is configured to be over-dimensioned in at least one of the anterior-posterior direction and medial-lateral direction relative to the rasped femur cavity. In one embodiment, the distance between diagonally opposite corner junctions of the shaft is substantially equal to the distance between corresponding diagonally opposite corner junctions of the femur cavity, so as to inhibit excess stress on the corticalis.

7 Claims, 11 Drawing Sheets

U.S. PATENT DOCUMENTS

| | | |
|---|---|---|
| 4,661,112 A | 4/1987 | Mueller |
| 4,664,668 A | 5/1987 | Beck et al. |
| 4,728,334 A | 3/1988 | Sportorno |
| 4,813,962 A | 3/1989 | Deckner et al. |
| 4,865,608 A | 9/1989 | Brooker, Jr. |
| 4,908,035 A | 3/1990 | Deckner et al. |
| 4,979,958 A | 12/1990 | Niwa et al. |
| 5,133,770 A | 7/1992 | Zweymuller et al. |
| 5,152,799 A | 10/1992 | Lyons |
| 5,456,717 A | 10/1995 | Zweymuller |
| 5,480,452 A | 1/1996 | Hofmann et al. |
| 5,507,833 A | 4/1996 | Bohn |
| 5,593,451 A | 1/1997 | Averill et al. |
| 5,593,452 A | 1/1997 | Higham et al. |
| 5,665,090 A * | 9/1997 | Rockwood et al. ............ 606/80 |
| 5,725,586 A | 3/1998 | Sommerich |
| 5,725,595 A | 3/1998 | Gustilo |
| 5,755,811 A | 5/1998 | Tanamal et al. |
| 5,928,289 A | 7/1999 | Deckner |
| 6,190,417 B1 | 2/2001 | Itoman et al. |
| 6,224,634 B1 | 5/2001 | Keller |
| 6,245,111 B1 | 6/2001 | Shaffner |
| 6,436,148 B1 | 8/2002 | DeCarlo et al. |
| 6,540,788 B1 | 4/2003 | Zweymuller |
| 6,808,539 B2 | 10/2004 | Zweymuller |

FOREIGN PATENT DOCUMENTS

| | | |
|---|---|---|
| DE | 23 24 865 | 5/1973 |
| DE | 26 27 569 A1 | 12/1977 |
| DE | 87 12607.9 | 9/1987 |
| DE | 38 19 948 | 6/1988 |
| DE | 90 06 893.9 | 6/1990 |
| DE | 41 29 724 A1 | 3/1993 |
| DE | 43 15 143 | 5/1993 |
| DE | 42 23 373 A1 | 1/1994 |
| DE | 94 02 934.2 | 10/1994 |
| DE | 295 06 036.0 | 4/1995 |
| DE | 297 05 500 U1 | 9/1998 |
| EP | 0 159 510 A2 | 10/1985 |
| EP | 0 159 510 A3 | 3/1987 |
| EP | 0 289 922 | 1/1988 |
| EP | 0 159 510 B1 | 5/1990 |
| EP | 0 700 670 A1 | 3/1996 |
| EP | 0 720 839 A1 | 7/1996 |
| EP | 0 821 923 | 7/1997 |
| EP | 1 044 665 A3 | 1/2001 |
| FR | 2 315 902 | 1/1977 |
| FR | 2 639 821 A1 | 12/1988 |
| FR | 2 634 642 | 2/1990 |
| FR | 2 681 239 | 9/1991 |
| FR | 2 699 398 | 12/1992 |
| WO | WO 00/59410 | 10/2000 |

OTHER PUBLICATIONS

Bohm, G., Lintner, F., Auterith, A., Lester D.K., Zweymuller, K., *Morphometric Examination of Straight, Tapered Titanium Stems*, Clinical Orthopaedics and Related Research, 2001, pp. 13-24, No. 393, Lippincott Williams & Wilkins, Inc.

Clements, J.P., Gheduzzi, S., Zweymuller, K., Lintner F., Schmotzer, H. Learmonth, I.D., Miles, A.W., *An In Vitro Cadaveric Biomechanical Evaluation of a Cementless Hip stem Comparison of Long and Short Term Stability*, 51$^{st}$ Annual Meeting of the Orthopaedic Research Society, 2005, Paper No. 0266, Centre for Orthopaedic Biomechanics, University of Bath, UK.

Osteonics Brochure for Omniflex-Ha™ Total Hip System, 1991, 8 pages.

Depuy, Inc. Brochure for the AML™ Femoral Component with Porocoat®, 1983, 2 pages.

Operating Technique Manual for the AML™ Total Hip System, available before Apr. 9, 2002, 32 pages.

Slide Presentation with Hip Stem Designs Available Before Apr. 9, 2002, 2 pages.

Office Action in U.S. Appl. No. 09/958,463, mailed Aug. 19, 2003.
Office Action in U.S. Appl. No. 09/958,463, mailed Mar. 1, 2004.
Office Action in U.S. Appl. No. 09/958,463, mailed Oct. 13, 2004.
Office Action in U.S. Appl. No. 09/958,463, mailed Apr. 18, 2005.
Office Action in U.S. Appl. No. 09/958,463, mailed Oct. 21, 2005.
Office Action in U.S. Appl. No. 09/958,463, mailed Jan. 25, 2006.
Office Action in U.S. Appl. No. 09/958,463, mailed Aug. 11, 2006.
Office Action in U.S. Appl. No. 09/958,463, mailed Jan. 23, 2007.
Office Action in U.S. Appl. No. 09/958,463, mailed Jul. 11, 2007.
Office Action in U.S. Appl. No. 11/432,914, mailed Aug. 22, 2007.

* cited by examiner

LEAFLIKE SHAFT OF A HIP-JOINT PROSTHESIS FOR ANCHORING IN THE FEMUR

CROSS-REFERENCE TO RELATED APPLICATIONS

This application is a continuation-in-part of U.S. patent application Ser. No. 10/355,385, filed on Jan. 30, 2003, now U.S. Pat. No. 7,175,668, which is a divisional of U.S. patent application Ser. No. 09/548,166, filed on Apr. 13, 2000, now U.S. Pat. No. 6,540,788.

BACKGROUND OF THE INVENTION

1. Field of the Invention

The invention relates to a leaf-like shaft of a hip-joint prosthesis for anchoring in the femur, with a femur-anchoring section and a prosthesis neck.

2. Description of the Related Art

Profiled shafts of this kind are generally known. As only a few examples in this regard reference is made to the patents EP 0 427 902 B1 or EP 0 244 610 B1 or U.S. Pat. No. 4,908,035.

As a rule the anchoring section of a shaft of the kind in question here is constructed with smooth surfaces. In EP 0 427 902 B1 it is proposed to construct one section of the shaft with contact surfaces provided with saw teeth. This measure is intended to improve fusion of the shaft to the bony substance.

It is disclosed in the patent CH-A 642 252 that the anterior and posterior leaf surfaces of the leaf part of a shaft are provided with groove-like indentations. However, bone tissue grows poorly into these. The tissue that fills up these indentations is generally a connective tissue with only slight stability.

SUMMARY OF CERTAIN INVENTIVE ASPECTS

In accordance with one aspect of the present invention, the femur-anchoring section of a leaf-like shaft is configured in such a way that the tissue growing onto the prosthesis consists to the greatest possible extent of spongy bone tissue, so as to ensure long-term, firm retention of the shaft in the femur.

This object is achieved by a leaf-like shaft with a femur-anchoring section that has an external contour in a plane perpendicular to the long axis that is substantially rectangular, and optionally includes recesses in the sides and/or at the corners and/or in the interior of the shaft.

In accordance with one embodiment, the femur-anchoring section of the shaft is substantially rectangular in cross section, so that in simplified (ignoring the tapering toward the tip) terms it is constructed as a "four-edged" profile, in particular as:

Oblique-cross profile;
H profile;
Double-H or -comb profile;
Rectangular hollow profile;
Rectangular facet profile;
Rectangular notch profile;
Approximately trapezoidal profile (with or without recesses at the sides or in the interior)
Or the like.

These profiles all exhibit, to a greater or lesser extent, the property that in the space between the anchoring section of the shaft and the wall of the surgically created cavity spongy bone tissue forms, so that revascularization of the bone occurs. The alternatives in accordance with the invention have the advantage that their periphery comprises substantially four edges, situated at the corners of a rectangle or trapezoid that extends perpendicular to the central axis of the shaft. This basic shape of the shaft has been found in practice to be particularly advantageous for the revascularization of the bone tissue.

It has further been found that a predetermined over-dimensioning of the side surfaces of the shaft in comparison to the "rasped" dimension ("null dimension")—with the exception of the edge regions, which should fit precisely—is advantageous in this respect, especially in the proximal section of the shaft.

With the further development in accordance with the embodiments described above, the revascularization of the bone tissue is additionally promoted, while on one hand the necessary stability or solidity of the shaft is preserved, but on the other hand the intervening space between shaft and operation-cavity wall is enlarged, with the result that a greater amount of new spongiosa is formed.

In accordance with one embodiment, a hip-joint endoprosthesis system is provided. The system comprises a rasp configured for forming a cavity in a femur, the cavity having substantially the same configuration as the rasp. The rasp has an anterior face, a posterior face generally opposite the anterior face, a lateral face, and a medial face generally opposite the lateral face. A distance between the anterior and posterior faces defines a first dimension, and a distance between the lateral and medial faces defines a second dimension. Each of the rasp faces is disposed adjacent another of the rasp faces, defining an edge therebetween. The system also comprises a shaft configured to be anchored in the cavity. The shaft has an anchoring section extending between a proximal region and a distal end of the shaft. The anchoring section defines an anterior face, a posterior face generally opposite the anterior face, a lateral face, and a medial face generally opposite the lateral face. A distance between the anterior and posterior faces defines a third dimension, and a distance between the lateral and medial faces defines a fourth dimension. Each of the shaft faces is adjacent another of the shaft faces, defining a junction therebetween, wherein the third dimension is greater than the first dimension.

In accordance with another embodiment, a hip-joint endoprosthesis system is provided. The system comprises a plurality of rasps configured for forming a cavity in a femur, the cavity having substantially the same configuration as the rasp used to form the cavity. Each rasp has an anterior face, a posterior face generally opposite the anterior face, a lateral face, and a medial face generally opposite the lateral face. A distance between the anterior and posterior faces defines a first dimension, and a distance between the lateral and medial faces defines a second dimension. Each of the rasp faces is disposed adjacent another of the rasp faces, defining an edge therebetween. The system also comprises a plurality of shafts, each of the shafts corresponding to one of the plurality of rasps. Each of the shafts is configured to be anchored in the cavity. Each shaft has an anchoring section extending between a proximal region and a distal end of the shaft. The anchoring section defines an anterior face, a posterior face generally opposite the anterior face, a lateral face, and a medial face generally opposite the lateral face. A distance between the anterior and posterior faces defines a third dimension, and a distance between the lateral and medial faces defines a fourth dimension. Each of the shaft faces is adjacent another of the shaft faces, defining a junction therebetween, wherein the third dimension of every shaft is greater than the first dimension of the corresponding rasp by a generally constant amount.

BRIEF DESCRIPTION OF THE DRAWINGS

Advantageous details of the prosthesis shaft in accordance with the invention are presented in the subordinate claims and explained in detail in the following description of exemplary embodiments with reference to the attached drawings, wherein

DETAILED DESCRIPTION OF CERTAIN INVENTIVE EMBODIMENTS

Figure 1:
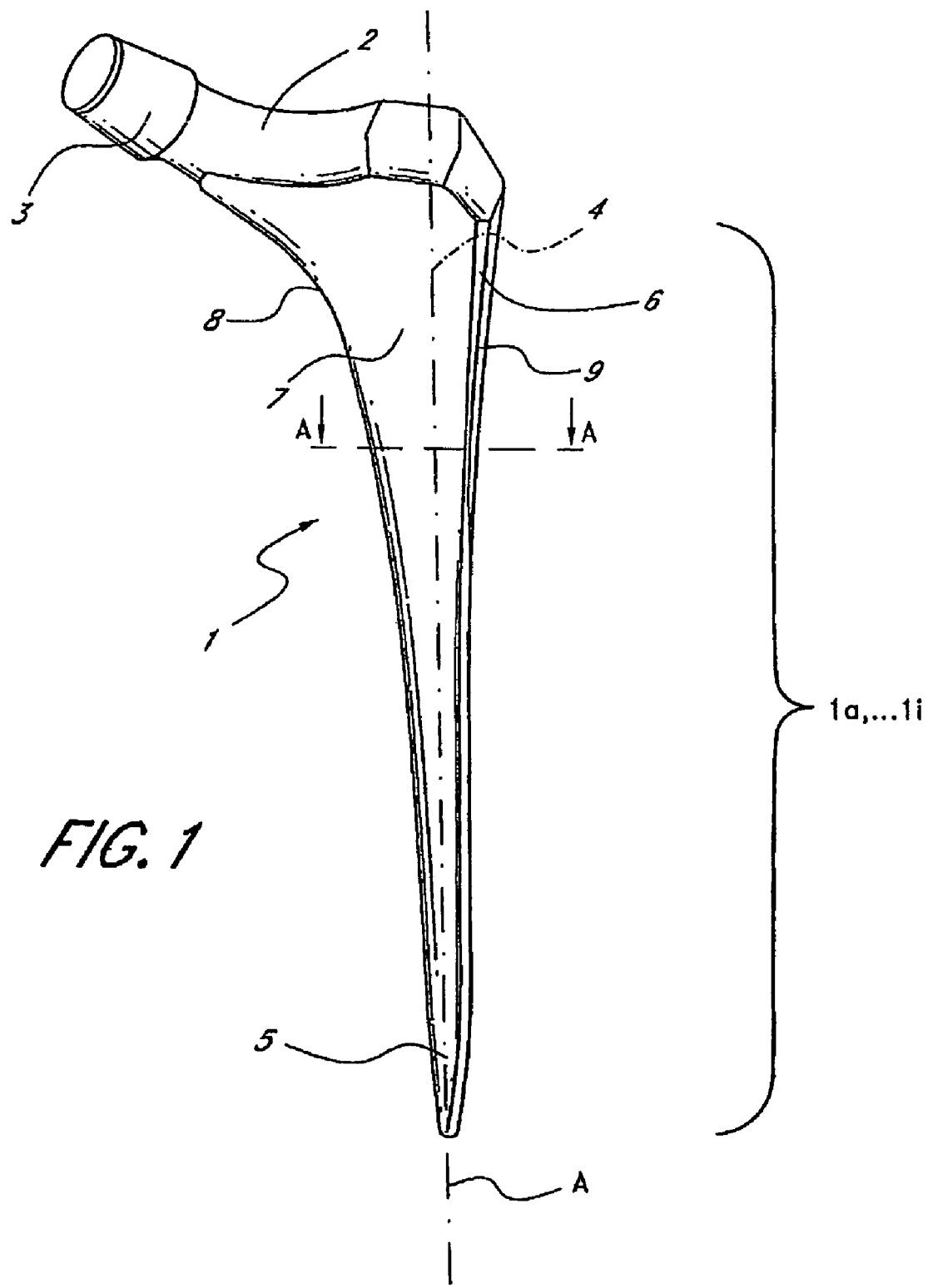
FIG. 1 is a perspective view of a leaf-like shaft, the femur-anchoring section of which is further developed in accordance with one embodiment.

FIG. 1 shows, in perspective, a leaf-like shaft 1 of a hip-joint prosthesis for anchoring in the femur. The exemplary embodiment shown here comprises an anchoring section $1a, \ldots 1i$ (see FIGS. 2 to 10), which expands conically on all sides from a distal end 5 to the proximal region, where on the medial side it merges with a continuously curving arch 8. This arch 8 is continuous with a prosthesis neck 2, onto which is set a conically tapering peg 3 which receives a spherical joint head. The prosthesis neck axis intersects the central long axis (not shown in FIG. 1) of the shaft and the anchoring section 1A . . . 1i at an angle that corresponds substantially to the angle between the neck and axis of the femur in a natural hip joint.

Laterally in the proximal region of the shaft 1 a trochanter wing 4 is formed, which is laterally delimited by a side surface 9. The transition between the lateral surface and the posterior or anterior surface is defined by a slanted edge 6 that extends from distal to proximal in the region of the trochanter wing 4. The "leaf" of the shaft 1 is defined in the proximal region and is identified by the reference numeral 7.

In FIGS. 2-10 various cross sections or profile shapes of anchoring sections $1a \ldots 1i$ of the shaft 1 are shown.

Figure 2:
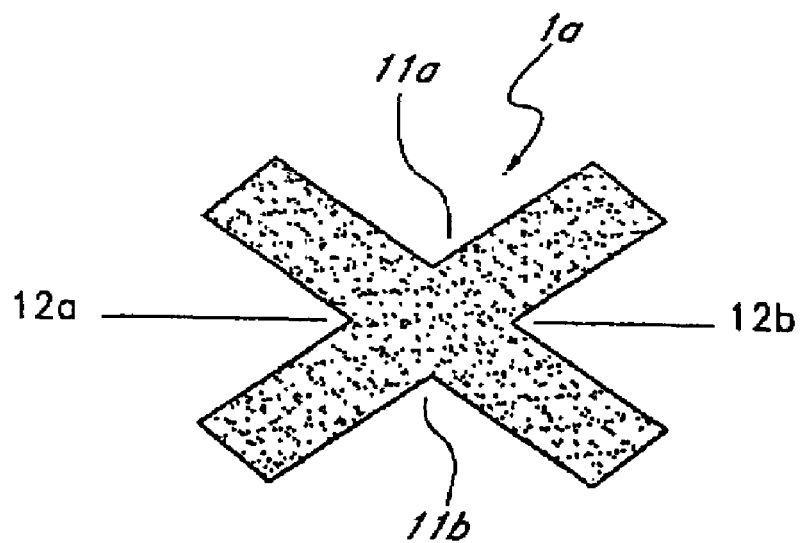
FIGS. 2-9 show various cross sections of the anchoring section of the shaft in FIG. 1 along the line A-A in FIG. 1.

According to FIG. 2, the anchoring section $1a$ is constructed as an oblique-cross profile, the limbs of which form V-shaped grooves $11a$, $11b$ on the anterior and posterior aspects respectively, each of which has an angle greater than 90°, and laterally and medially form V-shaped grooves $12a$, $12b$ with an angle smaller than 90°.

Figure 3:
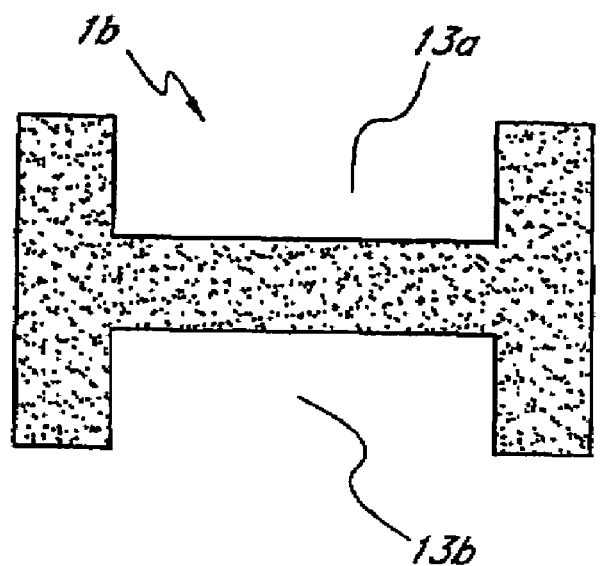

In the embodiment according to FIG. 3 the anchoring section $1b$ of the shaft 1 is constructed as an H profile. This profile comprises rectangular recesses $13a$, $13b$ on the posterior and the anterior aspect.

Figure 4:
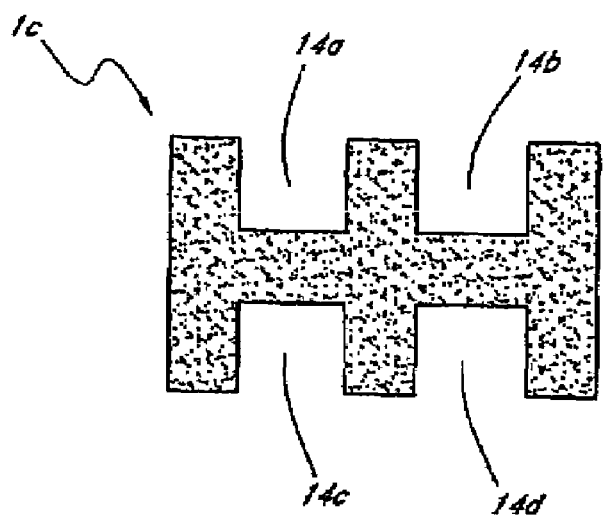

FIG. 4 shows another variant, in which the anchoring section $1c$ of the shaft 1 is a double-H profile or double-comb profile, in that rectangular longitudinal grooves $14a$, $14b$, $14c$, $14d$ are formed on the posterior and anterior aspects of the anchoring section.

Figure 5:
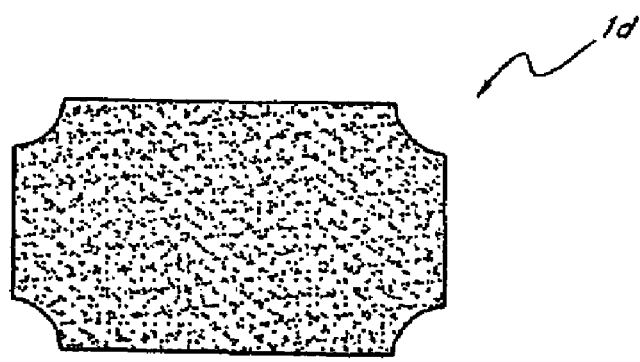

In the variant shown in FIG. 5, the anchoring section $1d$ of the shaft 1 is roughly rectangular in cross section, with concave facets formed at the four corners. In the illustrated embodiment, each of the facets between adjacent surfaces extends along a circular arc from one of the surfaces to one of the adjacent surfaces. Each facet preferably defines a quarter-circle between any two adjacent surfaces.

Figure 6:
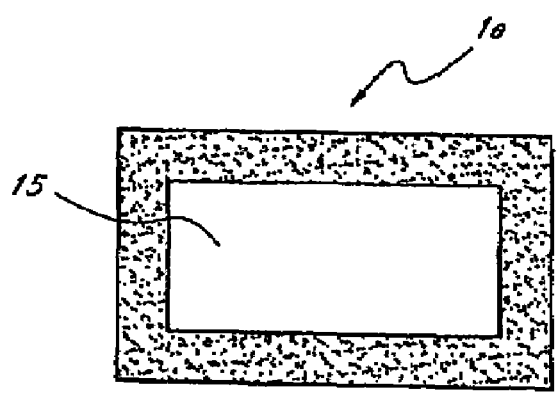
Figure 7:
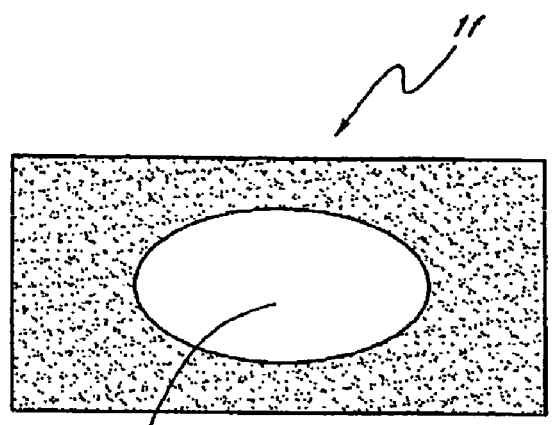

The embodiments according to FIGS. 6 and 7 comprise an anchoring section $1e$ and $1f$, respectively, in the form of a rectangular hollow profile, the embodiment according to FIG. 6 having a cavity 15 that is rectangular in cross section, whereas in the embodiment according to FIG. 7 the cross section of the cavity 16 is elliptical. These two variants are characterized by an especially high stability of the anchoring section, accompanied by low weight.

Figure 8:
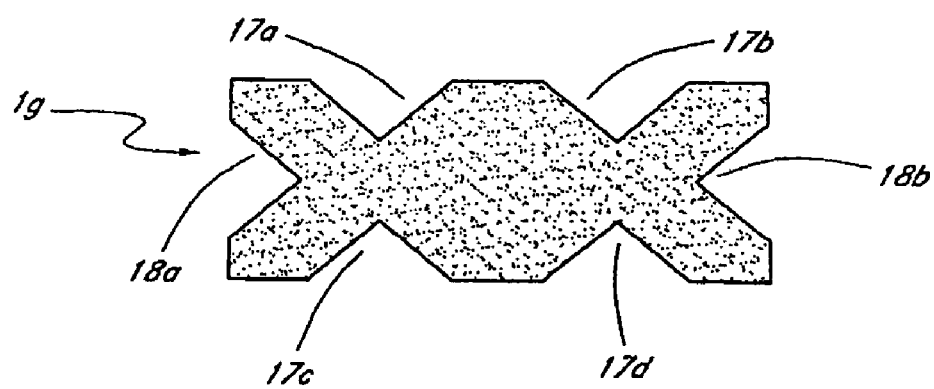

The variant according to FIG. 8 has an anchoring section $1g$ defined by a rectangular notched profile. On the anterior and on the posterior aspect there are formed two spaced-apart longitudinal notches $17a$, $17b$ and $17c$, $17d$ respectively. Each of these four notches is V-shaped. On the lateral and on the medial aspect one longitudinal notch $18a$, $18b$ is provided, which likewise are V-shaped notches or longitudinal grooves. The corners that delimit the outline of the anchoring section $1g$, like those in the embodiment according to FIGS. 6 and 7, can comprise flattened or concave facets like those shown in FIG. 5.

In the embodiment according to FIG. 6 the rectangular cavity 15 can be subdivided by a web or a cross-strut extending in the long direction of the shaft.

The embodiment according to FIG. 8, like that in FIG. 5, can be constructed as a hollow profile with a cavity that extends in the long direction of the shaft and has a circular or oval or elliptical cross section.

Figure 9:
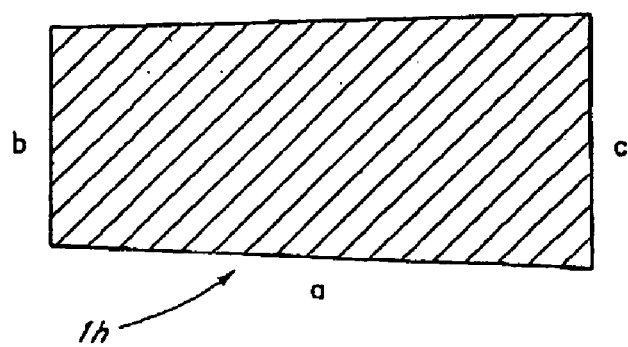

The embodiment of an anchoring section $1h$ shown in FIG. 9 differs from the embodiments in FIGS. 2-8 in having a trapezoidal cross section, which in this case is symmetrical with two equally long longer sides a in cross section, which correspond to the anterior and posterior surfaces, and two differently long shorter sides b, c, of which the shorter one is medial and the longer one lateral. This symmetrical trapezoidal shape is at present regarded as preferred, but in principle prosthesis shafts with asymmetrical trapezoidal cross sections can also be constructed.

The cross-sectional shapes shown in FIGS. 2-8 (which in those figures are, so to speak, inscribed within a rectangle) can also be modified to give them a basically trapezoidal shape: for instance, an asymmetrical oblique cross, an "H" with a longer and a shorter limb, an embodiment similar to that in FIG. 4 with three differently long limbs, an embodiment corresponding to FIG. 5 but with concave facets in the corner regions of a trapezoidal cross section, or various hollow profiles with a trapezoidal external configuration.

Figure 10:
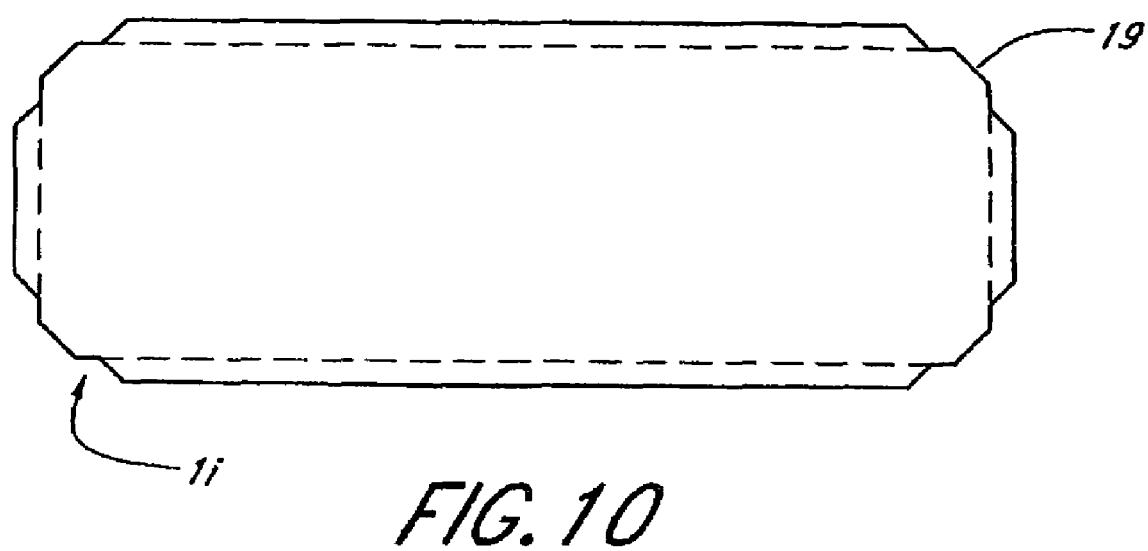
FIG. 10 shows another cross section of the anchoring section of the shaft in FIG. 1, in accordance with another embodiment.

In FIG. 10, to illustrate an additional special embodiment of the anchoring section of the shaft prosthesis in accordance with the invention, a cross-sectional shape is shown which again is basically rectangular and at all corners exhibits stepwise chamfered regions 19. The outer contour indicated by the dashed line approximately represents a conventional shaft cross section for the same application, with chamfered regions at an angle of 45° to the side surfaces. It is evident that the proposed new design (indicated by a continuous line) is over-dimensioned in comparison with this known embodiment over the greater part of all the side surfaces. However, all the chamfered regions have a middle section, the level of which coincides with the level of chamfering of the corresponding conventional prosthesis shaft. On either side of, and parallel to, this section are chamfered steps, set back slightly from the middle section.

This embodiment is based on the idea that it is advantageous for a prosthesis shaft—at least in its proximal region—to be over-dimensioned by a predetermined amount in comparison to the dimensions of the prepared cavity in the femur (i.e., in comparison to the "rasped dimension"), inasmuch as this over-dimensioning increases the pressure of the surfaces against the surrounding bone tissue and thus causes a degree of bone compression. In other words, one or both of a dimension between the medial and lateral surfaces and/or a dimension between the anterior and posterior surfaces is over-dimensioned with respect to the rasped dimension. When the ordinary forging precision is also taken into account, the over-dimensioning amounts to about 1-3% of the "rasped dimension" in the marrow space, which is also to be understood as the "null dimension". In another embodiment, the over-dimensioning is between about 5% and about 15% of the "rasped dimension" in the marrow space. In still another embodiment, the over-dimensioning is between about 8% and about 12% of the "rasped dimension" in the marrow space. In yet another embodiment, the over-dimensioning is about 10% of the "rasped dimension." In a preferred embodiment, the percentage over-dimensioning between the proximal region of the shaft and a corresponding proximal region of the rasped dimension is generally constant for a plurality of shaft sizes. Accordingly, the amount of over-dimensioning is less for smaller shafts, than for larger shafts.

In the corner regions (e.g. the diagonal dimensions) of the cross-section of the shaft, by contrast, the fit is preferably as precise as possible so as not to place the corticalis under excessive stress. That is, the diagonal distance of a cross-section of the shaft in the proximal region is generally equal to a corresponding diagonal distance in the rasped cavity. Therefore the corner regions are reduced to the exact rasped dimension just prior to implantation. A final shaping to produce the stepped corner configuration shown in FIG. 10 has proved to be relatively easy to accomplish and advantageously effective; in principle, however, other fine structures in the corner region are possible, with which the dimensional conformity of the corners (more precisely the chamfers) can be made consistent with an over-dimensioning of the remaining side and end surfaces—for example, rounding or additional chamfered regions at an angle to the main chamfer.

All the characteristics disclosed in the application documents are claimed as essential to the invention insofar as they are new to the state of the art individually or in combination.

Figure 11A:
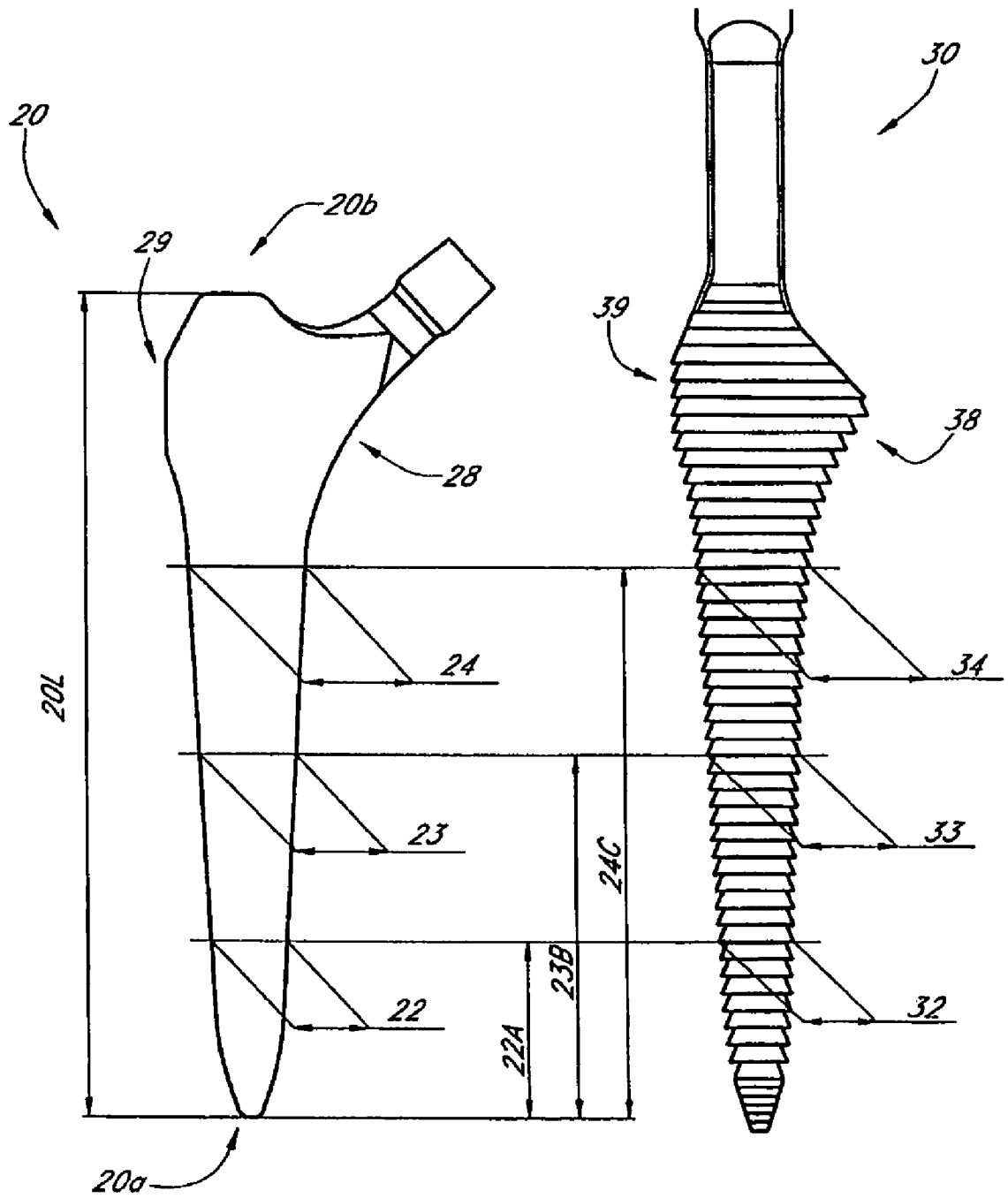
FIG. 11A is a side view of a conventional shaft and corresponding rasp.
Figure 11B:
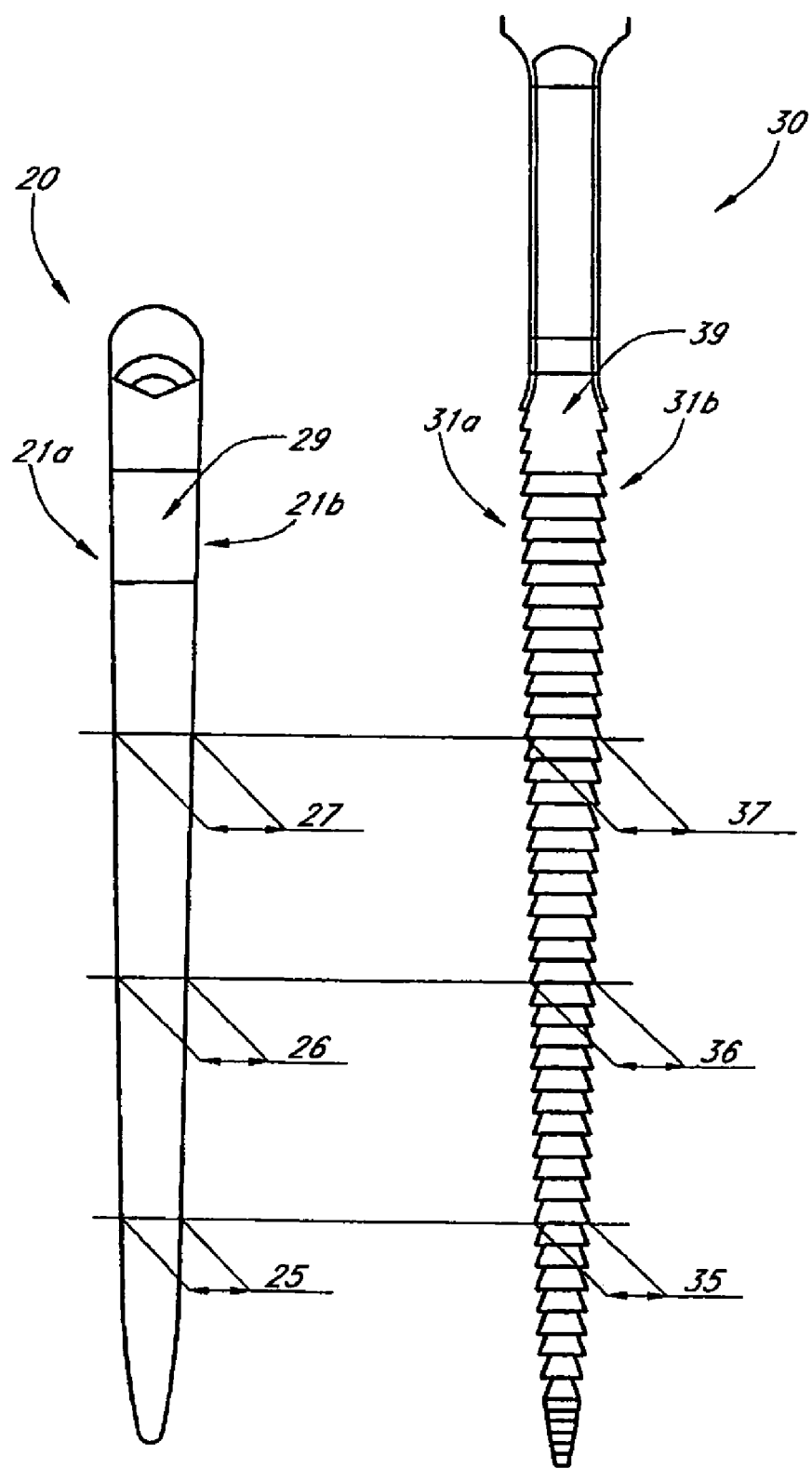
FIG. 11B is a front view of the conventional shaft and corresponding rasp shown in FIG. 11A.

In contrast with the embodiments discussed above, conventional prosthetic femoral shafts have dimensions substantially equal to those of the corresponding rasp used to form the femur cavity into which the femoral shaft is implanted. A particular size rasp is used for a particular size shaft, so that each prosthetic femoral shaft has a corresponding rasp. FIGS. 11A and 11B show different views of a conventional shaft 20 and a corresponding rasp 30 used to form the femur cavity (not shown) into which the shaft 20 is implanted. Preferably, the femur cavity has the same shape or configuration as the rasp 30. Accordingly, a description of the dimensions of the rasp 30 can be used to identify corresponding dimensions of the femur cavity.

As shown in FIG. 11A, the shaft 20 has a length 20L between the distal end 20a and the proximal end 20b of the shaft 20. The shaft 20 also defines an anterior side 21a (see FIG. 11B) and a posterior side 21b (see FIG. 11B), a curved medial side 28 and a lateral side 29. The corresponding rasp 30 also defines an anterior side 31a (see FIG. 11B), a posterior side 31b (see FIG. 11B), a generally curved medial side 38 and a lateral side 39 thereof. Preferably, the curved medial side 28 of the shaft 20 has the same contour as the curved medial side 38 of the rasp 30, such that when superimposed on each other, the curved medial sides 28, 38 of the shaft 20 and rasp 30 align with each other.

With continued reference to FIG. 11A, the tapering nature of the shaft 20 defines a width between a medial and lateral sides 28, 29 that varies along the shaft 20. The shaft 20 has a first width 22, a second width 23 and a third width 24 at a corresponding first distance 22A, second distance 23B and third distance 24C, respectively, from the distal end 20a of the shaft 20. The rasp 30 also has a first width 32, a second width 33 and a third width 34, which correspond to the first, second and third widths 22, 23, 24, respectively, of the shaft 20. In conventional shafts 20, the first width 22 can vary between about 9 mm and about 23 mm, the second width 23 can vary between about 11.5 mm and about 26.5 mm, and the third width 24 can vary between about 15 mm and about 31 mm. Additionally, in a conventional shaft-rasp combination, such as that shown in FIGS. 11A and 11B, the first, second and third widths 22, 23, 24 of the shaft 20 are equal to the first, second and third widths 32, 33, 34 of the rasp 30, respectively. Accordingly, conventional shafts 20 are not over-dimensioned in the lateral-medial direction relative to the femur cavity formed with the corresponding rasp 30.

Additionally, as shown in FIG. 11B, the tapering nature of the shaft 20 defines a width between the anterior and posterior sides 21a, 21b that varies along the shaft 20. The shaft 20 has a fourth width 25, a fifth width 26 and a sixth width 27 at the corresponding first distance 22A, second distance 23B and third distance 24C, respectively, from the distal end 20a of the shaft 20. The rasp 30 also has a fourth width 35, a fifth width 36 and a sixth width 37, which correspond to the fourth, fifth and sixth widths 25, 26, 27, respectively, of the shaft 20. In conventional shafts 20, the fourth width 25 can vary between about 6.5 mm and about 11.5 mm, the fifth width 26 can vary between about 7.5 mm and about 13 mm, and the sixth width 27 can vary between about 8.5 mm and about 14.5 mm. In a conventional shaft-rasp combination, such as that shown in FIGS. 11A and 11B, the fourth, fifth and sixth widths 25, 26, 27 of the shaft 20 are equal to the fourth, fifth and sixth widths 35, 36, 37 of the rasp 30, respectively. Accordingly, conventional shafts 20 are not over-dimensioned in the anterior-posterior direction relative to the femur cavity formed with the corresponding rasp 30.

Figure 12A:
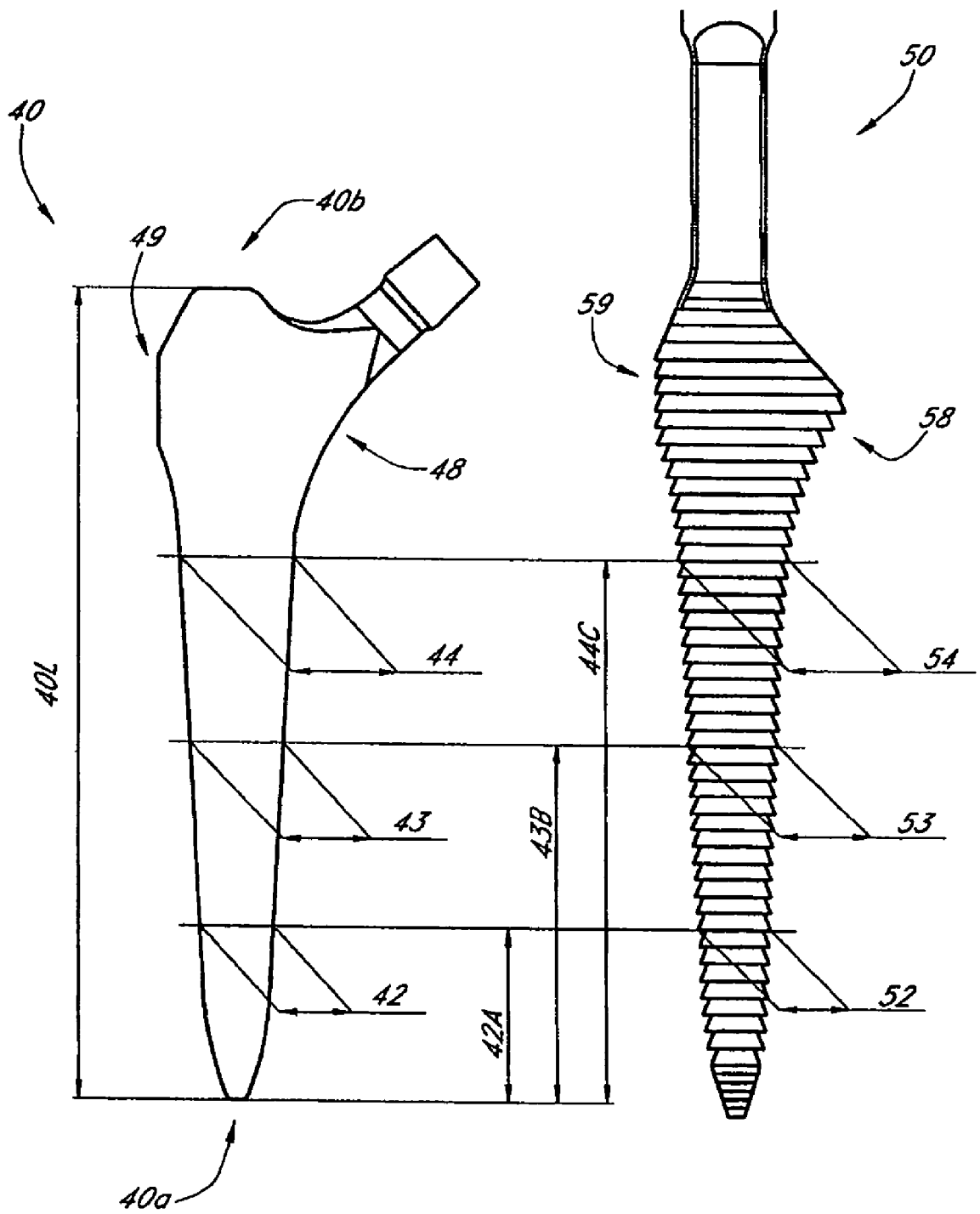
FIG. 12A is a side view of a shaft and corresponding rasp, according to one embodiment.
Figure 12B:
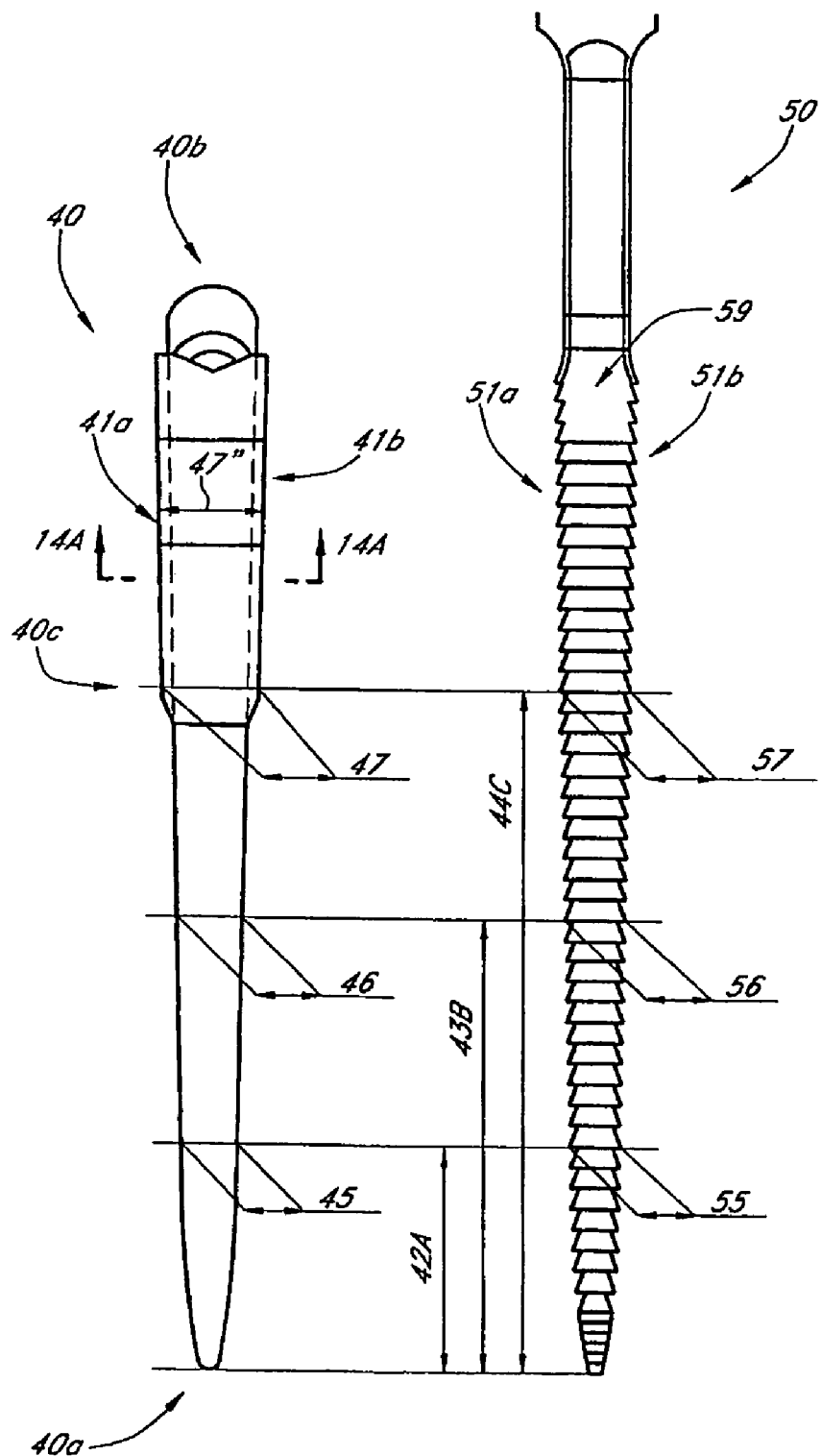
FIG. 12B is a front view of the shaft and corresponding rasp shown in FIG. 12A.

As discussed above, in at least one embodiment, the shaft is advantageously over-dimensioned, at least in a proximal region of the shaft, by a predetermined amount relative to a corresponding dimension of the rasped cavity. FIGS. 12A and 12B show different views of a prosthetic femoral shaft 40 and a corresponding rasp 50 used to form the femur cavity (not shown) into which the shaft 40 is implanted. Preferably, the femur cavity has the same shape or configuration as the rasp 50. Accordingly, the description below of the dimensions of the rasp 50 can be understood to apply to the dimensions of the femur cavity.

As shown in FIG. 12A, the shaft 40 has a length 40L between the distal end 40a and the proximal end 40b of the shaft 40. The shaft 40 also defines an anterior side 41a (see FIG. 12B) and a posterior side 41b (see FIG. 12B), a curved medial side 48 and a lateral side 49. The corresponding rasp 50 also defines an anterior side 51a (see FIG. 12B), a posterior side 51b (see FIG. 12B), a generally curved medial side 58 and a lateral side 59 thereof. Preferably, the curved medial side 48 of the shaft 40 has the same contour as the curved medial side 58 of the rasp 50. In one embodiment, when the shaft 40 and the rasp 50 are superimposed on each other, the curved medial sides 48, 58 of the shaft 40 and rasp 50 align with each other.

With continued reference to FIG. 12A, the tapering nature of the shaft 40 defines a width between a medial and lateral sides 48, 49 that varies along the shaft 40. The shaft 40 has a first width 42, a second width 43 and a third width 44 at a corresponding first distance 42A, second distance 43B, and third distance 44C, respectively, from the distal end 40a of the shaft 40. The rasp 50 also has a first width 52, a second width 53 and a third width 54, which correspond to the first, second and third widths 42, 43, 44, respectively, of the shaft 40. In one embodiment, the first, second and third widths 42, 43, 44 of the shaft 40 are equal to the first, second and third widths 52, 53, 54 of the rasp 50, respectively, so that the shaft 40 is not over-dimensioned in the lateral-medial direction relative to the femur cavity formed with the corresponding rasp 50. In another embodiment, the third width 44 of the shaft 40 is greater than the corresponding third width 54 of the rasp 50, such that the shaft 40 is over-dimensioned relative to the rasp 50 in a proximal region 40c of the shaft 40. In other embodiments, the shaft 40 can be over-dimensioned relative to the rasp 50 in other axial regions of the shaft 40 (e.g., the first width 42).

Additionally, as shown in FIG. 12B, the tapering nature of the shaft 40 defines a width between the anterior and posterior sides 41a, 41b that varies along the shaft 40. The shaft 40 has a fourth width 45, a fifth width 46 and a sixth width 47 at the corresponding first distance 42A, second distance 43B and third distance 44C, respectively, from the distal end 40a of the shaft 40. The rasp 50 also has a fourth width 55, a fifth width 56 and a sixth width 57, which correspond to the fourth, fifth and sixth widths 45, 46, 47, respectively, of the shaft 40. In the illustrated embodiment, the fourth and fifth widths 45, 46 of the shaft 40 are equal in dimension to the fourth and fifth widths 55, 56 of the rasp 50, respectively. However, the sixth width 47 of the shaft 40 is greater than the corresponding sixth width 57 of the rasp 50. Accordingly, the shaft 40 is over-dimensioned in the anterior-posterior direction relative to the rasped femur cavity in the proximal region 40c of the shaft 40. In the illustrated embodiment, the over-dimensioning in the anterior-posterior direction between the axial location of the sixth width 47 and the proximal end 40b of the shaft 40 is generally constant relative to a width 47", shown as dashed lines, that corresponds to the width of the rasped femur cavity formed by the rasp 50. Additionally, the shaft 40 is over-dimensioned in the anterior-posterior direction such that the anterior and posterior sides 41a, 41b extend generally parallel to each other.

Figure 13:
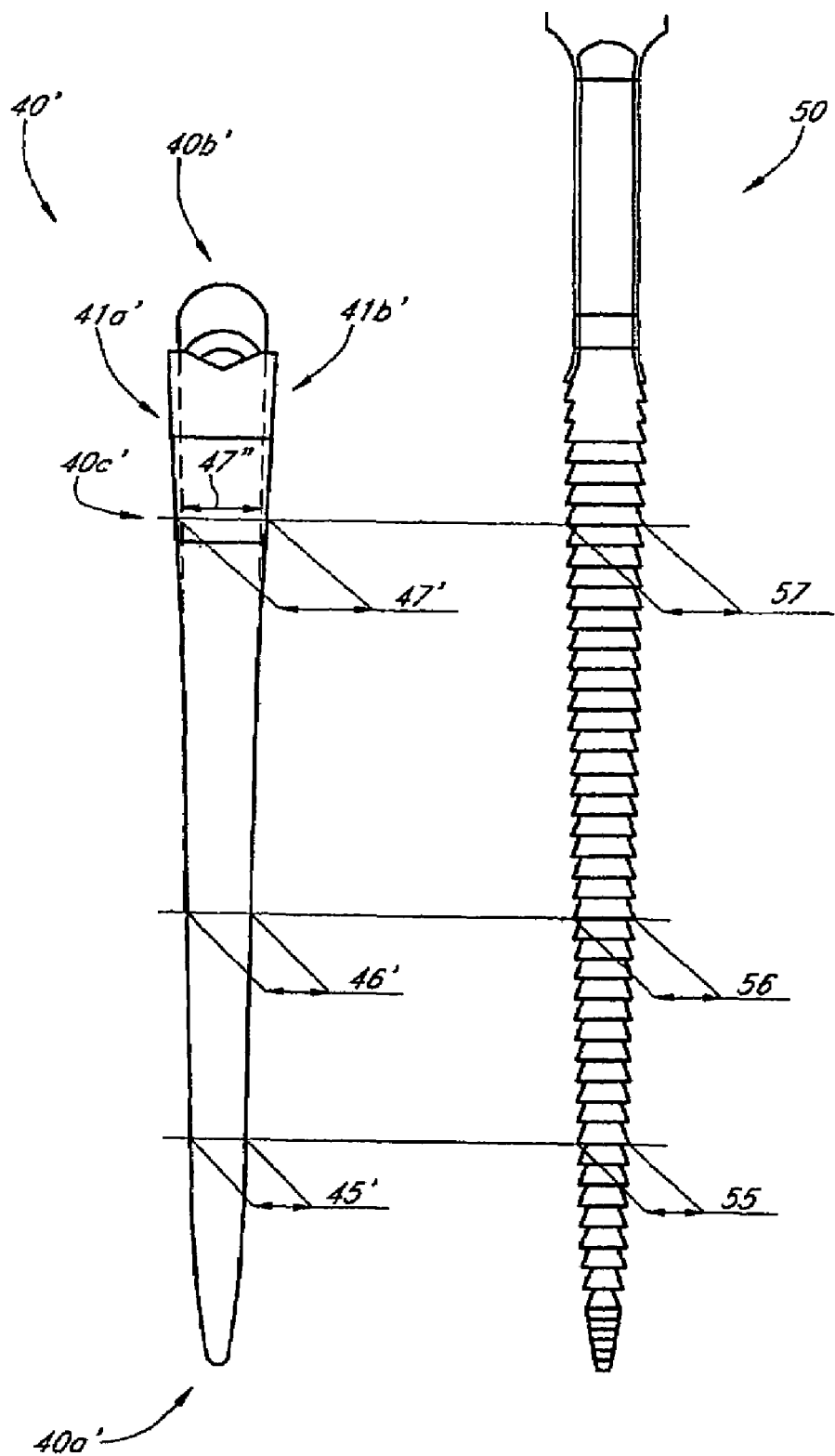
FIG. 13 is a front view of a shaft and corresponding rasp, according to another embodiment.

FIG. 13 shows another embodiment of a prosthetic femoral shaft 40'. The shaft 40' is similarly configured as the shaft 40 described above. Therefore, the same numerical identifies are used for the same sections in the shafts 40, 40', except that a "'" is used to identify the sections in the shaft 40'. The shaft 40' generally has the same medial-lateral configuration as the shaft 40, as shown in FIG. 12A.

As shown in FIG. 13, the fourth and fifth widths 45', 46' of the shaft 40' are equal to the fourth and fifth widths 55, 56 of the rasp 50, respectively. However, the sixth width 47' of the shaft 40', is greater than the corresponding sixth width 57 of the rasp 50. Accordingly, the shaft 40' is over-dimensioned in the anterior-posterior direction relative to the rasped femur cavity in the proximal region 40c' of the shaft 40'. In the illustrated embodiment, the over-dimensioning in the anterior-posterior direction between the axial location of the sixth width 47' and the proximal end 40b' of the shaft 40' increases toward the proximal end 40b' relative to a width 47", shown as dashed lines, that corresponds to the width of the rasped femur cavity formed by the rasp 50. Accordingly, the shaft 40' is over-dimensioned in the anterior-posterior direction such that the anterior and posterior sides 41a', 41b' extend generally at an acute angle relative to each other.

As discussed above, in one preferred embodiment the over-dimensioning of the shaft 40 relative to a femur cavity rasped with the corresponding rasp 50 is of between about 1% and about 3%. In another embodiment, the over-dimensioning is of between about 5% and about 15%. In still another embodiment, the over-dimensioning is of between about 8% and about 12%. In yet another embodiment, the over-dimensioning is of about 10%. Preferably, the percentage over-dimensioning is generally constant for all shaft sizes. Accordingly, the amount of over-dimensioning is less for smaller shafts, than for larger shafts.

Figure 14A:
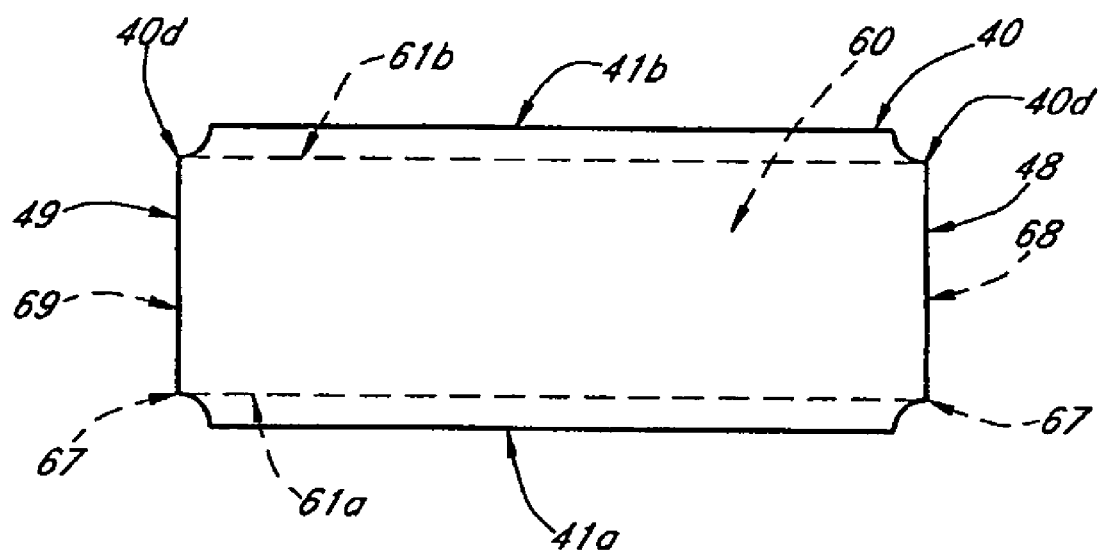
FIG. 14A shows a cross-section of the proximal region of the shaft in FIG. 12A superimposed on a cross-section of the rasped femur cavity formed with the corresponding rasp at the same axial location.

FIG. 14A shows a cross-section of the proximal region 40c of the shaft 40 in FIG. 12A, about line 14A-14A, relative to a cross-section of a femur cavity 60 formed with the rasp 50, prior to implantation of the shaft 40 in the cavity 60. In the illustrated embodiment, the shaft 40 has a generally rectangular cross-sectional shape with curved facets 40d at the corner junctions. However, in other embodiments, the shaft 40 can have any of the cross-sectional configurations discussed above. As shown in FIG. 14A, the femur cavity 60 has generally the same medial-lateral dimension as the shaft 40. That is, the distance between the lateral side 49 and the medial side 48 of the shaft 40, when superimposed on the cross-section of the rasped femur cavity 60, is the same as the distance between the medial side 68 and the lateral side 69 of the femur cavity 60. However, as shown in FIG. 14A, the shaft 40 is over-dimensioned in the anterior-posterior direction relative to the femur cavity 60. That is, the distance between the anterior side 41a and the posterior side 41b of the shaft 40, when superimposed on the cross-section of the rasped femur cavity, is greater than the distance between the anterior side 61a and the posterior side 61b of the femur cavity 60. Advantageously, the distance between diagonally opposite curved facets 40d of the shaft 40 is substantially equal to the distance between diagonally opposite corner junctions 67 of the rasped femur cavity 60, so as to inhibit placing excessive stress on the corticalis.

Figure 14B:
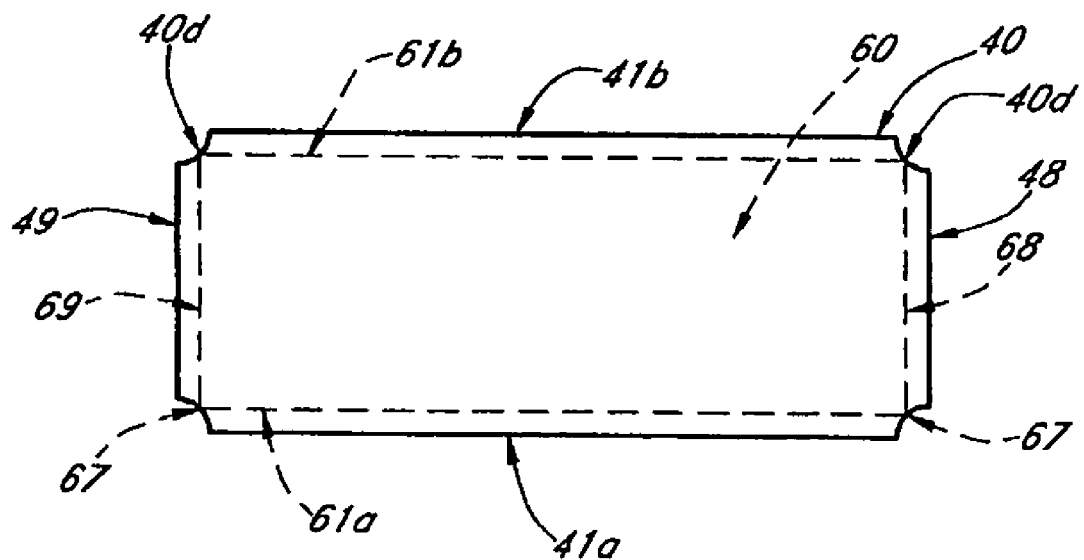
FIG. 14B shows a cross-section of the proximal region of the shaft in FIG. 12A superimposed on a cross-section of the rasped femur cavity formed with the corresponding rasp at the same axial location.

Though the embodiments described above with respect to FIGS. 12A-14A describe an over-dimensioning in the anterior-posterior direction of the shaft 40, 40', the shaft 40, 40' can alternatively, or additionally, be over-dimensioned in the medial-lateral direction. For example, FIG. 14B shows a cross-section of the proximal region 40c of the shaft 40, about line 14A-14A, relative to a cross-section of the femur cavity 60, where the shaft 40 is dimensioned such that the third width 44 is greater than the third width 54 of the rasp 50. That is, the shaft 40 is also over-dimensioned in the medial-lateral direction. In the illustrated embodiment, the shaft 40 has a generally rectangular cross-sectional shape with curved facets 40d at the corner junctions. However, in other embodiments, the shaft 40 can have any of the cross-sectional configurations discussed above. As shown in FIG. 14B, the femur cavity 60 has a medial-lateral dimension that is smaller than the corresponding medial-lateral dimension of the shaft 40.

That is, the distance between the lateral side 49 and the medial side 48 of the shaft 40, when superimposed on the cross-section of the rasped femur cavity 60, is greater than the distance between the medial side 68 and the lateral side 69 of the femur cavity 60. Additionally, as shown in FIG. 14B, the shaft 40 is also over-dimensioned in the anterior-posterior direction relative to the femur cavity 60. That is, the distance between the anterior side 41a and the posterior side 41b of the shaft 40, when superimposed on the cross-section of the rasped femur cavity 60, is greater than the distance between the anterior side 61a and the posterior side 61b of the femur cavity 60. Advantageously, the distance between diagonally opposite facets 40d of the shaft 40 is substantially equal to the distance between diagonally opposite corner junctions 67 of the rasped femur cavity 60, so as to inhibit placing excessive stress on the corticalis.

Although this invention has been disclosed in the context of a certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or subcombinations of the specific features and aspects of the embodiments may be made and still fall within the scope of the invention. Accordingly, it should be understood that various features and aspects of the disclosed embodiments can be combine with or substituted for one another in order to form varying modes of the disclosed invention. Thus, it is intended that the scope of the present invention herein disclosed should not be limited by the particular disclosed embodiments described above, but should be determined only by a fair reading of the claims.

What is claimed is:

1. A hip-joint endoprosthesis system comprising:
   a rasp configured for forming a cavity in a femur having substantially the same configuration as the rasp, the rasp having an anterior face, a posterior face generally opposite the anterior face, a lateral face, and a medial face generally opposite the lateral face, a distance between the anterior and posterior faces defining a first dimension, a distance between the lateral and medial faces defining a second dimension, each of the rasp faces disposed adjacent another of the rasp faces and defining an edge therebetween; and
   a shaft configured to be anchored in the cavity, the shaft having an anchoring section extending between a proximal region and a distal end of the shaft, the anchoring section defining an anterior face, a posterior face generally opposite the anterior face, a lateral face, and a medial face generally opposite the lateral face, a distance between the anterior and posterior faces defining a third dimension, a distance between the lateral and medial faces defining a fourth dimension, each of the shaft faces being adjacent another of the shaft faces and defining a junction therebetween said junction being a concave facet, wherein the third dimension is greater than the first dimension.

2. The system of claim 1, wherein the third dimension is over-dimensioned relative to the first dimension by between about 1% and 3%.

3. The system of claim 1, wherein the third dimension is over-dimensioned relative to the first dimension by between about 5% and 15%.

4. The system of claim 3, wherein the third dimension is over-dimensioned relative to the first dimension by between about 8% and about 12%.

5. The system of claim 4, wherein the third dimension is over-dimensioned relative to the first dimension by about 10%.

6. The system of claim 5, wherein the fourth dimension is substantially equal to the second dimension.

7. The system of claim 1, wherein a dimension between diagonally opposite edges of the rasp is substantially equal to a dimension between diagonally opposite junctions of the shaft.

* * * * *

UNITED STATES PATENT AND TRADEMARK OFFICE
CERTIFICATE OF CORRECTION

PATENT NO.        : 7,494,510 B2
APPLICATION NO. : 11/433067
DATED             : February 24, 2009
INVENTOR(S)       : Karl Zweymuller It is certified that error appears in the above-identified patent and that said Letters Patent is hereby corrected as shown below:

In column 1 at line 10 Change "7,175,668, which" to --7,175,668, which--.

In column 4 at line 32 Change "18bis" to --18b is--.

Signed and Sealed this

Thirtieth Day of June, 2009

JOHN DOLL
*Acting Director of the United States Patent and Trademark Office*